US011472762B2

(12) United States Patent
Krill et al.

(10) Patent No.: US 11,472,762 B2
(45) Date of Patent: Oct. 18, 2022

(54) PROCESS FOR PRODUCING ALKYL METHACRYLATES AND OPTIONALLY METHACRYLIC ACID

(71) Applicant: Röhm GmbH, Darmstadt (DE)

(72) Inventors: Steffen Krill, Muehltal (DE); Andreas Rühling, Darmstadt (DE); Florian Zschunke, Frankfurt (DE)

(73) Assignee: Röhm GmbH, Darmstadt (DE)

( * ) Notice: Subject to any disclaimer, the term of this patent is extended or adjusted under 35 U.S.C. 154(b) by 0 days.

(21) Appl. No.: 17/597,345

(22) PCT Filed: Jun. 10, 2020

(86) PCT No.: PCT/EP2020/066008
§ 371 (c)(1),
(2) Date: Jan. 4, 2022

(87) PCT Pub. No.: WO2021/004719
PCT Pub. Date: Jan. 14, 2021

(65) Prior Publication Data
US 2022/0204436 A1 Jun. 30, 2022

(30) Foreign Application Priority Data

Jul. 5, 2019 (EP) .................................... 19184618

(51) Int. Cl.
*C07C 51/25* (2006.01)
*C07C 45/35* (2006.01)
(Continued)

(52) U.S. Cl.
CPC ............. *C07C 51/252* (2013.01); *B01J 21/12* (2013.01); *B01J 21/14* (2013.01); *B01J 23/8913* (2013.01); *B01J 37/0201* (2013.01); *C07C 45/35* (2013.01)

(58) Field of Classification Search
None
See application file for complete search history.

(56) References Cited

U.S. PATENT DOCUMENTS

| 5,969,178 A | 10/1999 | Okamoto et al. |
| 7,012,039 B2 | 3/2006 | Watanabe et al. |
| 2010/0144931 A1* | 6/2010 | Balduf .................... C07C 41/42 422/600 |

FOREIGN PATENT DOCUMENTS

| EP | 1393800 | 3/2004 |
| EP | 2177267 | 4/2010 |

(Continued)

OTHER PUBLICATIONS

Nakamura et al., "Vapor Phase Catalytic Oxidation of Isobutene to Methacrylic Acid", Studies in Surface Sciences and Catalysis, vol. 7, 1981, pp. 755-767.

(Continued)

*Primary Examiner* — Colin W. Slifka
(74) *Attorney, Agent, or Firm* — Grüneberg and Myers, PLLC

(57) ABSTRACT

A novel process can be used for producing methacrylates such as methacrylic acid and/or alkyl methacrylates, in particular MMA. The process leads to an increased yield and increased efficiency compared to other C4-based production processes, in particular processes starting from isobutylene or tert-butanol as raw material. The process can be operated for longer periods without disruption and with the same or even increased activities and selectivities. The process can also be executed in a manner that is as simple, cost-effective, and environmentally friendly as possible.

13 Claims, 1 Drawing Sheet

(51) Int. Cl.
    *B01J 21/14*     (2006.01)
    *B01J 23/89*     (2006.01)
    *B01J 21/12*     (2006.01)
    *B01J 37/02*     (2006.01)

(56) References Cited

FOREIGN PATENT DOCUMENTS

| EP | 2210664 | 7/2010 |
|----|---------|--------|
| JP | 2003048863 | 2/2003 |
| WO | 2008/145418 | 12/2008 |

OTHER PUBLICATIONS

International Search Report dated Sep. 3, 2020 in PCT/EP2020/066008, with English translation, 6 pages.
Written Opinion dated Sep. 3, 2020 in PCT/EP2020/066008, with English translation, 10 pages.
Krill et al., "Produkte und Verfahren Viele Wege führen zum Methacrylsäuremethylester," Chem. Unserer Zeit, 2019, 53, 148-162.
English translation of Krill et al., "Produkte und Verfahren Viele Wege führen zum Methacrylsäuremethylester," ["Many Routes to Methyl Methacrylate"] Chem. Unserer Zeit, 2019, 53, pp. 148-162.

\* cited by examiner

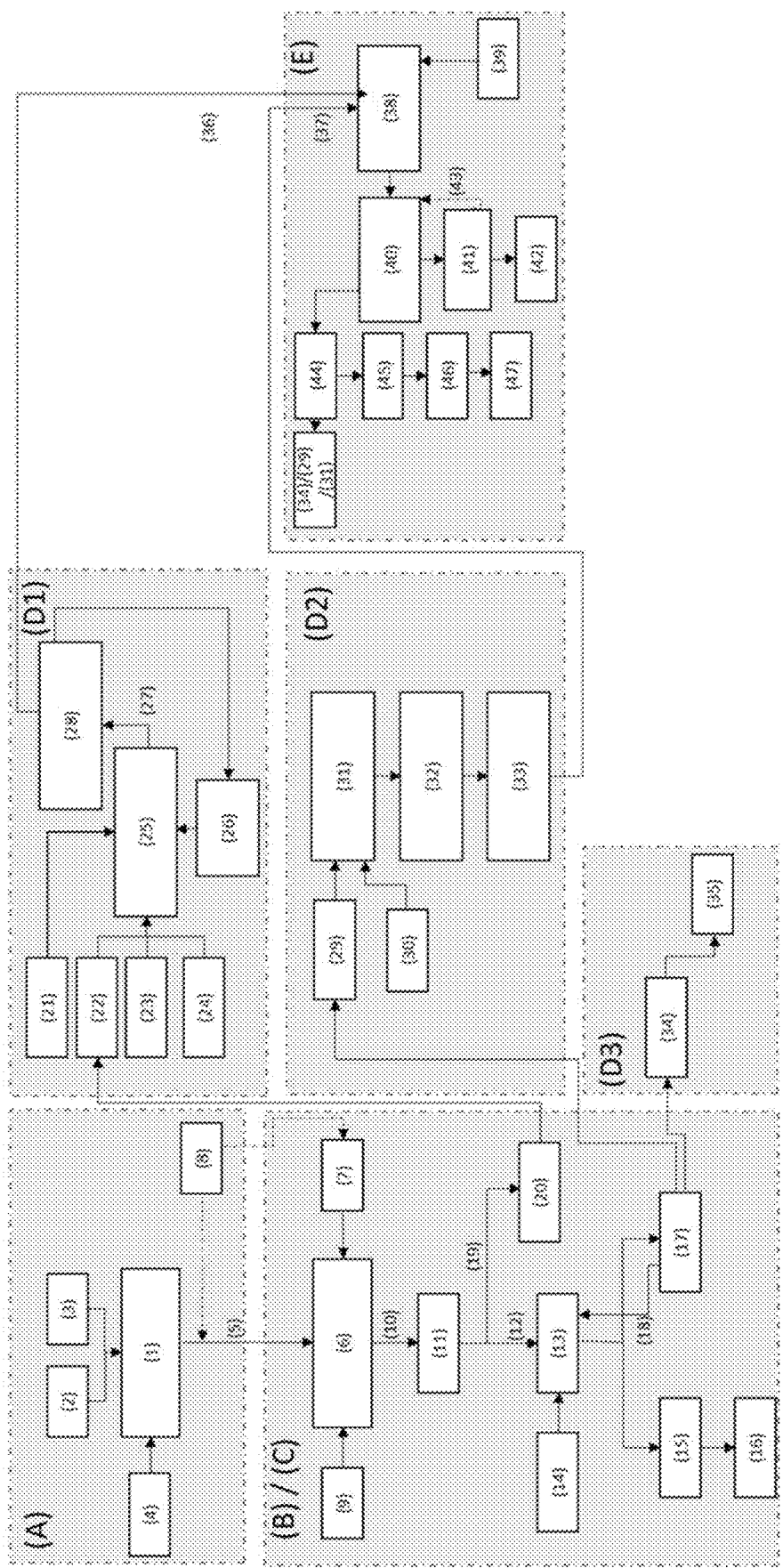

PROCESS FOR PRODUCING ALKYL METHACRYLATES AND OPTIONALLY METHACRYLIC ACID

CROSS-REFERENCE TO RELATED APPLICATIONS

This application is the National Stage entry under § 371 of International Application No. PCT/EP2020/066008, filed on Jun. 10, 2020, and which claims the benefit of priority to European Application No, 19184618.7, filed on Jul. 5, 2019. The content of each of these applications is hereby incorporated by reference in its entirety.

BACKGROUND OF THE INVENTION

Field of the Invention

The present invention relates to a novel process for producing methacrylates such as methacrylic acid and/or alkyl methacrylates, in particular MMA. In particular, the present invention relates to an increase in the yield and increase in the efficiency of C4-based production processes, that is to say in particular such processes starting from isobutylene or tert-butanol as raw material.

The present process according to the invention allows such processes to be operated for longer periods without disruption and with the same or even increased activities and selectivities. It also allows such processes to be executed in a manner that is as simple, cost-effective and environmentally friendly as possible.

Description of Related Art

Methyl methacrylate (MMA) is nowadays produced for example from hydrogen cyanide and acetone via the acetone cyanohydrin (ACH) formed as a central intermediate. This process has the disadvantage that enormous amounts of ammonium sulfate are obtained, the processing of which is associated with very high costs. Other processes based on the use of raw materials other than ACH have been described in the relevant patent literature and subsequently implemented on a production scale. C4-based raw materials such as isobutylene or tert-butanol are nowadays also used as feedstocks for this and are converted into the desired methacrylic acid derivatives over several process steps.

The first step here is generally the oxidation of isobutylene or tert-butanol to methacrolein, which is then converted into methacrylic acid with oxygen. The methacrylic acid obtained is then converted into MMA with methanol. Further details on this process are described inter alia in Ullmann's Encyclopedia of Industrial Chemistry 2012, Wiley-VCH Verlag GmbH & Co. KGaA, Weinheim, Methacrylic Acid and Derivatives, DOI: 10.1002/14356007.a16_441.pub2 and in Krill and Rühling et al. "Viele Wege führen zum Methacrylsäuremethylester" [Many routes lead to methyl methacrylate], Wiley-VCH Verlag GmbH & Co. KGaA, Weinheim, doi.org/10.1002/ciuz.201900869.

MMA processes based on C4 raw materials are in principle relevant as prior art for the present invention. A distinction is made on this basis between three processes for producing MMA. The raw materials used are, for example, tert-butanol, which is converted into isobutene through elimination of water, alternatively methyl tert-butyl ether, which is converted into isobutene through elimination of methanol, or isobutene itself, which is available as a raw material for example from a cracker. In summary, the following three routes result from this:

Process A "tandem $C_4$ direct oxidation" process without intermediate isolation of methacrolein: In a first step here, methacrolein is produced from isobutene, which is oxidized in a step 2 into methacrylic acid prior to final oxidation to MMA in a step 3.

Process B "separate C4 direct oxidation" process: The first step here is identical in that methacrolein is produced from isobutene, which undergoes initial isolation and intermediate purification in a step 2 prior to oxidation to methacrylic acid in step 3 and final esterification of this to MMA in a step 4.

Process C "direct metha process" or direct oxidative esterification process: In a first step here too, methacrolein is produced from isobutene, which here too undergoes initial isolation and intermediate purification in a step 2 prior to direct oxidative esterification to MMA in a step 3.

All described processes are well documented in the prior art, inter alia in (i) IHS Chemical Process Economics Program, Review 2015-05, R. J. Chang, Syed Naqvi (ii) Vapor Phase Catalytic Oxidation of Isobutene to Methacrylic Acid, Stud. Surf. Sci. Catal. 1981, 7, 755-767 (iii).

Re "tandem process", process A:

Isobutene is initially converted into methacrolein with air, optionally recycled gaseous streams and steam in the gas phase at temperatures between 300 and 400° C. in a shell-and-tube reactor on a contact having a bismuth-molybdenum basis similar to that of the Sohio process. The resulting process gas is temporarily cooled, mixed again with air and steam and mixed with recycled methacrolein from the second step. This gas mixture thus adjusted is converted directly into methacrylic acid at temperatures from 260 to 360° C. in a second shell-and-tube reactor containing a second contact comprising a modified heteropolyacid doped with other metal oxides. A characteristic feature of this process is that the first reaction needs to be operated with almost quantitative conversions, i.e. conversions of between 98 and 99.9% based on isobutene. This is necessary because the isobutene inhibits the activity of the subsequent oxidation. Moreover, the conversion of methacrolein in the second step is limited to 60 to 90%, with the result that substantial amounts of unreacted methacrolein are always still present in the process gas in the second step. The process gas in this second step is quenched and the methacrylic acid formed is separated from unreacted methacrolein. The unreacted methacrolein is condensed and re-evaporated in a concentrated, but impure form and fed back in between the two gas-phase reactors.

The tandem process thus gets its name from the fact that it is not the methacrolein from the process gas of the first step that is processed, but the recycled methacrolein from the second oxidation step.

Re "separate C4 direct oxidation process", process B:

Isobutene is initially converted into methacrolein with air, optionally recycled gaseous streams and steam in the gas phase at temperatures between 300 and 400° C. in a shell-and-tube reactor on a contact having a bismuth-molybdenum basis similar to that of the Sohio process. In this process, methacrolein is now cooled and condensed after exiting reactor 1. In addition, the methacrylic acid formed as a by-product is separated and the methacrolein is isolated by distillation. In this multistep operation, liquid methacrolein is obtained that must then be re-evaporated and is conditioned for the second oxidation step with steam and air, and optionally with recycle gas. At this point, recycled methacrolein is likewise now also fed in. This gas mixture thus adjusted is converted into methacrylic acid at temperatures of between 260 and 360° C. in a second shell-and-tube reactor containing a second contact comprising a modified heteropolyacid doped with other metal oxides. A characteristic feature of this process is thus that the first reaction is no longer able to be operated with quantitative conversions, but at an isobutene conversion of at least 90 to 98%. It is also advantageous that the reaction can be carried out up to a conversion having the maximum favourable combination of selectivity and yield of MAL from isobutene. Moreover, here too the conversion of methacrolein in the second step is limited to 60 to 90%, with the result that substantial amounts of unreacted methacrolein are always still present in the process gas in the second step. The process gas in this second step is quenched and the methacrylic acid formed is separated from unreacted methacrolein. The unreacted methacrolein is condensed and re-evaporated in a concentrated, but impure form and fed back in before the second gas-phase reactor. The "separate C4 direct oxidation" process gets its name from the fact that the methacrolein and the recycled methacrolein from the second oxidation step are processed and undergo intermediate isolation from the process gas of the first stage.

What processes A and B have in common is that methacrylic acid is the main product. The methacrylic acid obtained in varying degrees of purity in the two processes can optionally be reacted with methanol in an esterification reaction to form methyl methacrylate. This last step normally uses a Brønsted active catalyst, which in the homogeneous variant can be a dissolved strong acid, such as sulfuric acid or methanesulfonic acid, or it can be an acidic ion exchanger having corresponding heterogeneous acid functions.

Process C, the "direct metha process", proceeds in analogous manner to process B in the first two steps. After gas-phase oxidation of isobutene or tert-butyl alcohol, crude methacrolein is processed in liquid form. This is followed by an appreciably different step that is characteristic for this variant, the so-called direct oxidative esterification of methacrolein with methanol and an oxygen-containing gas, such as air, which is carried out in the liquid phase on a heterogeneous noble metal contact in powder form. The process provides MMA directly and does not proceed via the intermediate step of methacrylic acid production in the gas phase, as is the case in process A or B.

This process, developed by ASAHI, is described inter alia in documents U.S. Pat. Nos. 5,969,178 and 7,012,039. A particular disadvantage of this process is very high energy requirement.

U.S. Pat. No. 5,969,178 describes a process for the oxidative conversion of isobutene or tert-butanol to methacrolein and the subsequent oxidative esterification to MMA. In this second step, a liquid mixture of methacrolein and methanol with a reduced water content is reacted with molecular oxygen and a palladium catalyst, with the latter normally present as a supported palladium-lead catalyst. In U.S. Pat. No. 6,040,472, a Pd—Pb catalyst of this kind having an optimal palladium content of 5% results in an MMA selectivity of up to 91% and in a space-time yield of 5.3 mol MMA/h*kg catalyst.

However, palladium(-lead) catalysts have the disadvantage that high losses of lead component (so-called leaching) occur during continuous operation. Not only does this result in a costly disposal of waste water, it also means that the system must be continuously topped up with lead salts.

EP 2 177 267 and EP 2 210 664 describe the oxidative esterification of aldehydes to esters using nickel oxide catalysts having a gold content of between 1 and 80 mol % that are present on a support material. These catalysts are used in a diameter of between 10 and 200 µm. In particular, these particles are present in a shell structure in which the nickel oxide is present on the surface and the gold is present on an internal layer. These catalysts result at best in an MMA selectivity of up to 97.1% at a space-time yield of 9.6 mol MMA/h*kg catalyst.

EP 2 210 664 discloses a specific variant thereof in which catalyst particles in the nanometer range are loaded on a support particle having a diameter of between 10 and 200 µm. In one variant, this support particle has a size of 3 mm. The catalyst may also be present in a cylindrical structure or in honeycomb form in a fixed-bed reactor. Moreover, the process control in such a reactor variant is not described.

EP 1 393 800 describes a catalyst comprising gold particles or gold-containing particles having a diameter of less than 6 nm on a support material, in particular on a metal oxide. MMA selectivities of up to 93% and space-time yields of up to 50.7 mol MMA/h*kg catalyst are obtained using catalyst particles having a gold content of 4.5 mol %. The disclosed content is, moreover, analogous to that of EP 2 210 664.

Methacrylic acid is formed as the by-product of the MAL synthesis and the pH of the reaction mixture decreases accordingly. This causes further problems. Thus, as the pH decreases, increasing amounts of the by-product 1,1-dimethoxyisobutene (DMI) form as the acetal from methacrolein and methanol. This means that a fraction of the methacrolein that is present in the form of a dimethyl acetal is no longer available for further conversion into MMA and the space-time yield of the MMA synthesis falls accordingly. The dimethyl acetal also causes problems in the subsequent processing of the MMA by distillation. In addition, a mixture having a pH that is too low adversely affects the stability and lifetime of the catalyst used (leaching, alteration of the catalyst pore structure, etc.). Thus, with regard to the lower limit of pH 5, JP 2003048863 teaches that a basic solution may be added to correct the pH. This basic solution, for example in the form of a NaOH solution, itself normally has a pH higher than 10.

All these processes concern synthetic routes starting from C4 raw materials (isobutene or tert-butyl alcohol).

For these variants (processes A, B and C), it can be summarized that the prior art is beset by multiple technical and commercial deficiencies and deficits. For example, the twofold gas-phase oxidation achieves a yield of about 75-85% per process step. This means that an overall yield of methacrylic acid is only a scant 65% (t 5%). This is true overall for all embodiments, for example the so-called tandem processes, as are described on an industrial scale by Nippon Kayaku and Mitsui for example, but also for embodiments with intermediate isolation of methacrolein, as described by Mitsubishi Rayon.

There are also a considerable technical challenge with these processes concerning the safety of its implementation. In the evaporation of the so-called recycle methacrolein, that is to say methacrolein that is unreacted in the second oxidation step, and of the injection thereof between the two oxidation reactors, the process is operated in the so-called "lean" range very close to the explosion limit of the mixture. If this critical mixture is loaded with the process gas from the first reactor step, for example at temperatures normally over 300° C., this results in the formation of tarry deposits and problematic compositions of the feed gas upstream of the second oxidation reactor. This problem is described in a large number of patents and proposed solutions and can be counteracted only by means of complex and costly measures. Inadequate compensation of the problem is moreover a particular problem with continuous operation.

In summary, it can be stated that no process based on a C4 raw material has thus far been described in which the critical step of separation and reaction of unreacted methacrolein in the process gas from the second reaction, generally catalysed with a heteropolyacid, does not result in this recyclable methacrolein being fed back into the second heteropolyacid-catalysed oxidation. The only processes known from the prior art are thus ones in which this recyclable methacrolein is converted into methacrylic acid, with all the described disadvantages and technical problems as regards yield and the safety of implementation of recycling upstream of the second step. It was therefore particularly desirable to develop a highly efficient technology that permits this recycle methacrolein to be converted into methyl methacrylate without this having to be done via methacrylic acid.

There is thus above all a considerable need for improvements in the oxidative conversion of the recycle methacrolein in these C4-based processes.

What all these processes based on C4 starting materials have in common is that the oxidative steps to methacrylic acid subsequent to the production of MAL are relatively inefficient and none of the embodiments permit a final yield of more than 70%. There is therefore a great need for alternative process control with which a significant increase in efficiency is possible. Moreover, some of the by-products of the C4 processes result in deposits in the equipment. Depending on the by-product, these deposits can occur directly or they can occur through polymerization of a relatively reactive by-product. Here too, there is the need to reduce the overall amount of by-products formed, in particular of those that can form problematic deposits.

SUMMARY OF THE INVENTION

The object of the present invention was to provide a novel process for producing alkyl methacrylates, in particular MMA, that starts from C4 structural units and has a particularly high overall yield.

A further object of the present invention was to achieve an overall very high overall conversion of the reactants while keeping the amounts of waste generated as low as possible.

It was additionally an object of the present invention to produce an alkyl methacrylate, in particular MMA, having only minimal concentrations of specific by-products.

It was moreover the object of the present invention to achieve a process that allows different alkyl methacrylates and/or methacrylic acid to be very flexibly produced in a continuous process and on an industrial scale, and even at the same time if desired.

Other objects not explicitly mentioned can arise from the description of the invention hereinbelow, without being explicitly listed here.

The objects are achieved by a novel process for producing alkyl methacrylates and optionally methacrylic acid, in particular methyl methacrylate (MMA), from C4 raw materials, especially in a process having methacrolein as an intermediate.

The basis of the process according to the invention is a process in which, in a first reaction step in a reactor 1, methacrolein is produced through a partial oxidation in the gas phase and, in a second reaction step in a reactor 2, this is converted by a partial oxidation in the gas phase to methacrylic acid. The development according to the invention is characterized in that the unreacted methacrolein in reactor 2 is, in the second reaction step, separated from the methacrylic acid formed and, in a further oxidation step in a reactor 4, is oxidatively esterified in the liquid phase in the presence of an alcohol.

In addition, the crude methacrylic acid formed in reactor 2 is purified by distillation and/or extraction and/or, in a further step, reacted with an alcohol in a reactor 3 under acid catalysis to form the alkyl methacrylate.

BRIEF DESCRIPTION OF THE DRAWING

The FIGURE shows a diagram of the equipment components for executing the process of the invention.

DETAILED DESCRIPTION OF THE INVENTION

Preference is given to a variant of the process according to the invention in which the process comprises the following process steps:

A) producing methacrolein from isobutene and/or tert-butanol in the presence of steam and oxygen in a reactor 1, wherein the reaction takes place in the gas phase on a heterogeneous contact I, and wherein a methacrolein-containing process gas 1 is obtained.

B) transferring the process gas 1 from process step A), which contains methacrolein and steam, from reactor 1, with supply of an oxygen-containing gas and optionally additional steam, to a reactor 2, wherein a reaction on a heterogeneous contact II takes place and a methacrylic acid-containing, in particular methacrylic acid-rich, and methacrolein-containing, process gas 2 is obtained.

C) separating the process gas 2 from process step B) by condensation or quenching, extraction and/or distillation into a phase 3a comprising methacrylic acid and a liquid phase 3b comprising methacrolein.

D1) oxidatively esterifying the methacrolein in the phase 3b obtained from process step C) in a reactor 4 with an alcohol in the presence of an oxygen-containing gas and a heterogeneous noble metal-containing oxidation catalyst comprising metals and/or metal oxides, wherein a mixture comprising an alkyl methacrylate, unreacted alcohol, methacrylic acid and unreacted methacrolein is obtained as a liquid process stream 4.

D2) esterifying, under acid catalysis, the methacrylic acid in the optionally additionally purified phase 3a obtained from process step C) with an alcohol in a reactor 3 on a contact III, and D3) cleaning steps for isolating the methacrylic acid obtained in phase 3a, including at least one distillation.

Further preferably, the methacrolein-containing process gas 1 is after step A) purified by means of at least one distillation and/or extraction before it is used as purified condensate and, after evaporation, as a component of the process gas 1 in process step B).

In a particular variant of the present invention, the oxygen-containing gas stream in process step B) or D1) is a partially recycled gas stream. In the process, it is also possible for both named gas streams to be a partially recycled gas stream.

In the oxidative esterification reaction according to step D1), preference is given to using a heterogeneous oxidation catalyst. Particularly preferably, this catalyst is characterized in that it comprises one or more preferably ultrafinely divided metals having an average particle size of <20 nm. This is particularly the case when the catalyst contains gold as an active component of the oxidation catalyst. When using particular catalysts that contain palladium or platinum as an active component, these components are no longer necessarily nanoscale or smaller than 20 μm, but are also present in the form of relatively large aggregates. However, the palladium- and platinum-containing contacts normally have higher loads of noble metal than is the case for example in gold-based contacts. It has been found to be particularly advantageous when these metals are noble metals such as palladium. The metals are particularly preferably selected from the group consisting of gold, palladium, ruthenium, rhodium and silver. It is usual, but not mandatory, for only one of these metals to be used. It is similarly preferable to carry out the reaction in step D1) in the liquid phase at a pressure of 1 to 100 bar.

Similarly preferably and particularly in combination with the catalyst mentioned above, the heterogeneous oxidation catalyst used in the oxidative esterification reaction according to step D1) comprises one or more, preferably ultrafinely divided metals, in particular noble metals on one or more support materials based on silica, alumina, titanium dioxide, magnesium oxide, bismuth oxide, tellurium oxide, or other basic oxides from the groups of the alkali metals and alkaline earth metals, wherein the resulting support material has a diameter from 10 μm to 10 mm.

Particularly active variants of these catalysts are those that, in addition to the noble metal component, include one or more further elements or oxides thereof selected from the group consisting of manganese, iron, cobalt, nickel, copper, zinc, lead, the lanthanoids (atomic number 57 to 71), tellurium, antimony and bismuth.

Known catalysts are based for example on oxidic supports containing palladium-lead, gold-nickel, gold-cobalt or palladium with a mixture of tellurium, antimony and bismuth.

It is very preferable when steps A) to D1) and also D2) are carried out in a continuous process. This can optionally also be done with regard to step D3), wherein the latter can also be executed on a batchwise basis in an otherwise continuous process. With regard to D3), it would alternatively also be conceivable to divert a substream of phase 3*a* and for methacrylic acid to be isolated from this substream in accordance with D3) in a manner that is preferably flexibly adjustable and executed on a continuous or batchwise basis.

The process according to the invention is on an industrial scale particularly relevantly employable when the alcohol in process step D1) is methanol. In this embodiment, the oxidative esterification reaction according to step D1) is preferably carried out with a molar ratio of methanol to methacrolein in the stationary reaction phase in the range from 1:1 to 50:1.

Independently thereof, but preferably in combination, the reaction according to step D1) is carried out in the liquid phase at a pressure in the range from 2 to 50 bar, a pH in the range from 3 to 10 and at a temperature in the range from 10 to 200° C.

The alcohols in process steps D1) and D2) may be different. In such an embodiment, two different methacrylic esters are accordingly obtained that can be separately isolated and purified. It is however preferable when the alcohol in process steps D1) and D2) is in each case the same alcohol, particularly preferably methanol. Such an embodiment has, in particular, the advantage that the two product streams from D1) and D2) can be combined and processed together.

Particularly preferably, the crude products of process steps D1) and D2) are purified directly from reactors 4 and 3 or are combined and purified together after in each case one or two optional separate purification steps.

Particularly when the process is operated continuously, it has proved advantageous when the respective organic phases from process steps D1) and D2) are purified separately in at least one distillation step and/or one extraction step before they are combined. Because of very different by-product characteristics, a more efficient process design may be one in which processing is initially carried out separately. Thus, it may be advantageous for example to first separate the product of step D1) from low-boiling by-products and reactants, in particular methacrolein and methanol, and to for example feed them back into reactor 4, which ultimately results in a higher overall yield. On the other hand, by-products or reactants from process step D2), in particular methacrylic acid, can cause a lot of problems in continuous operation in process step D1) and can, for example, permanently damage the catalyst.

For the reactor discharge from D2), on the other hand, separate processing would be only of lesser benefit. However, since more by-products and reactants are present here, purification normally requires more steps than for the product of step D1). It can therefore be advantageous here if, upstream of combining the two product streams, the high boilers and then the low boilers are successively removed from the crude product of step D2) before the two product streams are combined for further processing.

In summary, the process according to the invention results in various advantages over prior art processes.

The process according to the invention affords a surprisingly high overall yield compared with known processes for producing alkyl methacrylates such as MMA starting from C4 structural units. This is particularly the case given that the only partially reacted methacrolein from step B) is isolated in step C) and converted very efficiently in step D1). Whereas step D1) is inherently more expensive to operate than steps C) and D2), since relatively costly noble metal-based catalysts are normally used for D1).

This also results in an overall very high total conversion of the reactants and accordingly relatively small amounts of waste.

It was also surprisingly found that the combination of two separate routes for producing the MMA results overall in only minimal concentrations of specific by-products being present in the end product. Even though the total amount of by-products should be comparable, the concentration of individual substances is nonetheless relevant, for example to the colour of the end product and of polymers produced therefrom, to the storage stability or to an inhibitory effect during a polymerization.

Moreover, the process according to the invention surprisingly allows the very flexible simultaneous production, in a continuous process and on an industrial scale, of two different alkyl methacrylates and additionally even—via a substream—methacrylic acid.

Specific Aspects of the Process

In accordance with the process, the generation of recycle MAL and the conditioning thereof is a prerequisite for setting important, critical or relevant concentrations of methacrolein itself and of process-specific by-products. The synthesis of recycle MAL is described briefly hereinbelow in relation to the current prior art.

In a first shell-and-tube reactor, isobutene or tert-butanol is oxidized to methacrolein at temperatures of between 320 to over 400° C. at a slight overpressure in the presence of atmospheric oxygen and steam, as is recycle gas. Conversion in the tandem process is greater than 98% and tends to be lower in the "separate C4 direct oxidation" process. The residence time in the reactor containing modern doped bismuth-molybdate contacts is normally 1 to 4 seconds. This can be ascertained, for example, from U.S. Pat. No. 5,929,275. GHSV values of between 1000 and 2000 s$^{-1}$ are obtained. The exiting process gas phase is mixed with a cooler recycle MAL gas phase together with atmospheric oxygen and steam. This results in the feed gas for the second step. As in the first step, the second oxidation step is operated at a moderate overpressure of between 0.1 and 2 bar and at temperatures of between 260 and 360° C. Heteropolyacid contacts based on molybdenum and phosphorus and some further dopants are used for this purpose (see in this regard e.g. US2007/0010394). The modified heteropolyacids still show a strong dependence between selectivity and conversion. This is the case insofar as significantly poorer selectivities tend to be achieved at higher conversions. The conversion, and the associated catalyst loading, is consequently set at between 65 and 85%. For all processes and modifications thereof, this means it is necessary to separate unreacted methacrolein present in the process gas from the desired product, methacrylic acid, and ultimately to feed it back upstream of the second oxidation reactor as a so-called recycle MAL.

Depending on the nature of the catalyst and on the process control parameters, the methacrolein-containing mixture separated from the methacrylic acid after the second reaction step contains, besides methacrolein, other by-products such as inter alia aldehydes that can undergo reaction in an oxidative esterification (DOE). The methacrolein-containing mixture is referred to hereinafter as recycle MAL.

As prior art, the following limits can be defined for the by-product spectrum of the recycle MAL:

| | |
|---|---|
| 0.5-4% by weight | acetaldehyde |
| 1-8% by weight | acetone |
| 1-5% by weight | acrolein |
| 0.05-0.4% by weight | butane-2,3-dione |
| 0.2-1.5% by weight | MMA |
| 1-5% by weight | water |
| 1-5% by weight | methacrylic acid |
| 0.1-3% by weight | acetic acid |
| 70-95% by weight | methacrolein |

A characteristic feature of the recycle MAL, depending on the process (tandem or intermediate isolation of MAL), is a methacrolein content of more than 70% by weight alongside a content both of lower-boiling components, such as acetone, acrolein and acetaldehyde, and higher-boiling components such as MMA, water and methacrylic acid.

As aldehydes obtainable in the oxidative esterification in step D1), acrolein and acetaldehyde should be mentioned here. Moreover, the methacrylic acid and any other acids such as acetic acid present in the inflow of reactor 4 result in a greater requirement of base in order to adjust the pH for the oxidative esterification to the desired value. In the separation of methacrylic acid from recycle methacrolein, it is therefore desirable to adjust the methacrylic acid concentration in the recycle methacrolein to the lowest possible value prior to evaporation.

In the process according to the invention, besides the conversion of the recycle methacrolein to MMA in a direct oxidative esterification to MMA, very particular preference is also given to the separation of recycle methacrolein from methacrylic acid present in the process gas of the second gas-phase reaction. The hot process gas 2 from step B normally exits the reactor at 250 to 360° C. and must first be cooled. It is normally initially cooled to a temperature of between 150-250° C. via a recuperative gas cooler. Recuperative gas coolers are preferred, because they allow the heat to be used for steam generation. The gas phase, the temperature of which has now been lowered, is then passed into a circulating condensed quench phase usually at temperatures of between 50 and 100° C. This quench phase may be the bottoms section of a quench column that is circulated and thermostated via a pump. At the head of this quench column most of the methacrolein passes over in gaseous form together with the process gas, whereas most of the methacrylic acid formed is condensed and quenched in the bottoms. In a subsequent step in the process, methacrolein condenses and is absorbed together with water. In this step, the recycle methacrolein is obtained in liquid form together with all condensable secondary components such as low boilers. Despite this, an effective separation from the process gas that escapes at the head of this column is achieved. In a final step, methacrolein is now desorbed from the absorber phase, affording the recycle methacrolein that has a purity of more than 70% by weight. For example, a crude recycle methacrolein is thus produced that can now be fed into the direct oxidative esterification. It was surprisingly found that the by-products present in the recycle methacrolein, in particular reactive low boilers such as acrolein and acetaldehyde and also other components, generally also react without substantial effects on the selectivity of the main reaction or on catalyst performance in a way that allows reaction by-products to be effectively separated from the desired MMA.

Thus, acrolein can react to form methyl acrylate, acrylic acid, acrolein dimethyl acetal, methyl 3-methoxypropionate, methyl 3-hydroxypropionate, methyl 2-hydroxypropionate or hetero-Diels-Alder products of two acroleins, which may be present as the free acid or the methyl ester.

Acetaldehyde can react further to acetic acid or methyl acetate.

In addition to the desired product MMA, methacrolein can also react further, for example to methacrylic acid, which is unwanted in the mixture with MMA. Other possible by-products can be, in addition, the acetal dimethoxyisobutene, methyl 3-methoxyisobutyrate, methyl 3-hydroxyisobutyrate, methyl 2-hydroxyisobutyrate or also here the corresponding hetero-Diels-Alder products, which for simplicity are referred to here as di-MAL acid and di-MAL ester.

In addition, the removal of butane-2,3-dione (so-called diacetyl) after the DOE is necessary, because diacetyl in the polymerization of MMA to PMMA causes yellowing of the otherwise transparent PMMA products. Diacetyl originates from the two gas-phase oxidation reactions and is carried over into the DOE with the feedstock recycle methacrolein. Even in trace amounts well below 1% by weight, diacetyl can result in discoloration in subsequent polymers. The DOE largely does not itself result in the formation of any additional diacetyl.

The DOE for the recycle MAL may be carried out with various alcohols and provides the corresponding carboxylic esters from the aldehydes in the recycle MAL and the alcohol employed. Preference is given to using methanol as the alcohol. Alternatively, a di-, tri- or tetra-functional alcohol may also be employed. The polyfunctional carboxylic esters obtained are known as crosslinkers. A particularly preferred example of a difunctional alcohol is ethylene glycol.

The DOE may be carried out in a batchwise or continuous process, with continuous operation particularly preferred.

The reaction may here be carried out in various types of reactor known to those skilled in the art. Examples thereof, which are not limiting, include stirred-tank reactors, bubble-column reactors, fluidized-bed reactors, tubular reactors, shell-and-tube reactors, fixed-bed reactors, trickle-bed reactors and all combinations thereof. Very particularly preferably, the catalyst is, during the DOE, used in a stirred reactor in suspension form (as a slurry).

The following examples document the possibility of using the recycle MAL in a DOE.

EXAMPLES

Example 1—Preparation of the Catalyst Support—Silica-Alumina-Magnesium Oxide A 250 ml beaker is charged with 21.36 g of $Mg(NO_3)_2 \cdot 6H_2O$ together with 31.21 g of $Al(NO_3)_3 \cdot 9H_2O$ and dissolved in 41.85 g of demineralized water while stirring with a magnetic stirrer. To this is then added, with stirring, 1.57 g of 60% $HNO_s$. 166.67 g of silica sol (Köstrosol 1530AS from Bad Köstritz, 30% by weight of $SiO_2$, average particle size: 15 nm) is weighed into a 500 ml three-necked flask and cooled to 15° C. with stirring. To the sol is added slowly, with stirring, 2.57 g of 60% $HNO_3$. The nitrate solution is added to the sol, with stirring, at 15° C. over a 45-min period. At the end of the addition, the mixture is heated to 50° C. over a 30-min period and stirred at this temperature for a further 24 h. At the end of this time, the mixture is spray-dried at an outlet temperature of 130° C. A thin layer of the dried powder (spherical, average particle size 60 μm) is heated to 300° C. in a Naber oven over a 2-h period, held at 300° C. for 3 h, heated to 600° C. over a 2-h period and finally held at 600° C. for 3 h.

Example 2—Preparation of the Catalyst—AuCoO@Silica-Alumina-Magnesium Oxide

A suspension of 10 g of $SiO_2$—$Al_2O_3$—MgO of the support from example 1 in 33.3 g of demineralized water is heated to 90° C. and stirred at this temperature for 15 min. To this suspension is added, with stirring, a solution of $Co(NO_3)_2 \cdot 6H_2O$ (569 mg, 1.95 mmol) in 8.3 g of water preheated to 90° C. At the end of the addition, the mixture was stirred at 90° C. for a further 30 min. This suspension is mixed, with stirring, with a solution of 0.52 ml of 1 M NaOH solution preheated to 90° C. Immediately thereafter, a solution of $HAuCl_4 \cdot 3H_2O$ (205 mg) in 4.3 g of water heated to 90° C. is added. At the end of the addition, the suspension is stirred for a further 30 minutes, cooled to room temperature and filtered. The filter cake is washed with demineralized water until the conductivity has fallen below 100 μS/cm. The material is dried at 105° C. for 10 hours, the agglomerates are gently crushed and it is then heated to 450° C. over a 1 hour period, calcined at this temperature for 5 hours and cooled to room temperature.

For all the examples hereinbelow, the composition of the recycle MAL was as follows:

| | |
|---|---|
| 2.0% by weight | acetaldehyde |
| 5.5% by weight | acetone |
| 3.5% by weight | acrolein |
| 0.2% by weight | diacetyl |
| 1.2% by weight | MMA |
| 4.0% by weight | water |
| 2.9% by weight | methacrylic acid |
| 0.2% by weight | acetic acid |
| 80% by weight | methacrolein |

Other organic constituents are present in a content of less than 0.1% by weight each and in a total content of less than 2.5% by weight.

Example 3—Batch Test

The catalyst obtained in example 2 (384 mg), recycle MAL (1.20 g, 80% by weight of MAL) and methanol (9.48 g) were suspended in a 140 ml steel autoclave with a magnetic stirrer. The pH of the recycle MAL was 4.8 and was stabilized with 100 ppm of Tempol. The autoclave was pressurized to an overpressure of 30 bar with a gas mixture of 7% $O_2$ in $N_2$. The explosion limit of the mixture is 8% by volume of oxygen. The autoclave was heated to 60° C. for 2 hours, cooled, vented and the suspension was filtered. The filtrate was analysed by GC. The conversion of MAL was 17.9%, the selectivity for MMA was 73.3% and the space-time yield was 2.78 mol MMA/kg catalyst per hour.

Despite suboptimal parameter control and the absence of pH regulation during the reaction, the suitability in principle of the DOE for the reaction of recycle MAL is recognized.

Example 4—Batch Test

The catalyst obtained in example 2 (384 mg), recycle MAL (1.20 g, 80% by weight of MAL) and methanol (9.48 g) were suspended in a 140 ml steel autoclave with a magnetic stirrer. The pH of the recycle MAL was first adjusted to 7.0 with 1% NaOH in MeOH and stabilized with 100 ppm of Tempol. The autoclave was pressurized to an overpressure of 30 bar with a gas mixture of 7% by volume of $O_2$ in $N_2$. The explosion limit of the mixture is 8% by volume of oxygen. The autoclave was heated to 60° C. for 2 hours, cooled, vented and the suspension was filtered. The filtrate was analysed by GC. The conversion of MAL was 28.9%, the selectivity for MMA was 75.6% and the space-time yield was 4.29 mol MMA/kg catalyst per hour.

Example 5—Batch Test

The catalyst obtained in example 2 (384 mg), recycle MAL (1.20 g, 80% by weight of MAL) and methanol (9.48 g) were suspended in a 140 ml steel autoclave with a magnetic stirrer. The pH of the recycle MAL was first adjusted to 7.0 with 1% NaOH in MeOH and stabilized with 100 ppm of Tempol. The autoclave was pressurized to an overpressure of 30 bar with a gas mixture of 7% by volume of $O_2$ in $N_2$. The explosion limit of the mixture is 8% by volume of oxygen. The autoclave was heated to 80° C. for 2 hours, cooled, vented and the suspension was filtered. The filtrate was analysed by GC. The conversion of MAL was 67.0%, the selectivity for MMA was 89.5% and the space-time yield was 11.1 mol MMA/kg catalyst per hour.

Example 6—Batch Test

The catalyst obtained in example 2 (384 mg), recycle MAL (1.20 g, 80% by weight of MAL) and methanol (9.48 g) were suspended in a 140 ml steel autoclave with a magnetic stirrer. The pH of the recycle MAL was first adjusted to 7.0 with 1% NaOH in MeOH and stabilized with 100 ppm of Tempol. The autoclave was pressurized to an overpressure of 30 bar with a gas mixture of 7% by volume of $O_2$ in $N_2$. The explosion limit of the mixture is 8% by volume of oxygen. The autoclave was heated to 60° C. for 4 hours, cooled, vented and the suspension was filtered. The filtrate was analysed by GC. The conversion of MAL was 47.3%, the selectivity for MMA was 83.9% and the space-time yield was 8.1 mol MMA/kg catalyst per hour.

Example 7—Continuous Operation

Recycle MAL (80% by weight of MAL) and methanol are mixed so as to obtain a molar ratio of 1 to 4 (MAL to MeOH). The solution is adjusted to pH 7.0 with stirring and cooling and stabilized with 100 ppm of Tempol. A steel autoclave (400 ml) is filled with catalyst from the example (20 g, 7% by weight) and methanol. The autoclave is equipped with 2 continuous filters, a gas-entrainment stirrer and a bubbler. The reactor is closed, pressurized to 4 bar with air and heated to 80° C. The continuous delivery of the recycle MAL was adjusted so as to obtain a loading of 11 mol MAL/kg catalyst per hour. The pH was maintained at a constant 7.0 by addition of 1% by weight NaOH in methanol. The reaction was operated for 500 hours and the continuously collected product samples analysed by GC every 24 hours. The conversion of MAL was 69%, the MMA selectivity was 93.5% and the space-time yield was 7.1 mol MMA/kg catalyst per hour. After 500 hours, no catalyst deactivation was able to be observed and the reactor showed no impurities or build-up of polymer deposits. Besides MMA, the principal by-products detected in the mixture were methacrylic acid in a selectivity of 3.1% and 2.4% of methyl 3-methoxyisobutyrate. Other identified by-products were methyl acrylate and methyl acetate. Acetone and diacetyl, which were already present in the recycle MAL stream, did not react under these conditions in as much as they were measurable.

The examples, in particular example 7, show that, compared with the prior art for the utilization of recycle MAL, the process according to the invention brings appreciable advantages in respect of yield and costs and is at the same time more environmentally friendly.

LIST OF REFERENCE NUMBERS

The FIGURE shows a diagram of the equipment components for executing the process of the invention. In the context of the invention, individual embodiments may deviate from this exemplary illustration.
(A) Synthesis and isolation of methacrolein ((1)-(5))
(1) Reactor 1 for C4 oxidation (process step A)
(2) Steam inflow
(3) Oxygen/air inflow line
(4) Isobutene and/or tert-butanol inflow
(5) Transfer of process gas 1 to reactor 2
(B) Oxidation of methacrolein to methacrylic acid and (C) separation of MAA and MAL ((6)-(20))
(6) Reactor 2 for C4 oxidation (process step A)
(7) Oxygen/air inflow line
(8) Optional joint compression and purification of the recycle gas for (5) and (7)
(9) Optional steam inflow
(10) Discharge from reactor 2=process gas 2
(11) Quenching and/or condensing of process gas 2. Separation of process gas 2 into a liquid methacrylic acid-containing phase 3 (into (13)) and into a gaseous methacrolein-containing phase 4 (into (20))
(12) Liquid methacrylic acid-containing phase 3
(13) Extraction with organic extractant
(14) Inflow line for organic extractant (normally heptane inflow)
(15) Aqueous phase of the extraction
(16) Waste-water treatment
(17) Organic phase of the extraction with the crude methacrylic acid
(18) Recycling of organic extractant
(19) Gaseous methacrolein-containing phase 4
(20) Purification of methacrolein by absorption/desorption
(D1) Oxidative esterification of methacrolein to an alkyl methacrylate and recycling of the methacrolein ((21)-(27))
(21) Inflow line for alcohol (normally methanol inflow)
(22) Supply of methacrolein, optionally with further distillation to remove low boilers
(23) Oxygen/air inflow line
(24) Base inflow
(25) Reactor 4 for oxidative esterification of methacrolein
(26) Methacrolein/alcohol mixed phase for recycling into reactor 4
(27) Discharge from reactor 4 (23)
(28) Distillation column for separating methacrolein and some of the alcohol from crude alkyl methacrylate (D2) Esterification of methacrylic acid to an alkyl methacrylate ((29)-(33))
(29) Optional further purification of phase 3 to remove low boilers
(30) Inflow line for alcohol (normally methanol inflow)
(31) Reactor 3 for esterification of methacrylic acid to an alkyl methacrylate
(32) Optional distillation of the discharge from reactor 3 (24) to remove high boilers
(33) Optional distillation of the discharge from reactor 3 (24) to remove low boilers (D3) Isolation of methacrylic acid ((34)-(35))
(34) Distillation of crude methacrylic acid
(35) Optional further processing of methacrylic acid
(E) Example for the processing of the crude alkyl methacrylate (e.g. crude MMA) ((36)-(47))
(36) Inflow for the crude alkyl methacrylate from process step D1
(37) Inflow for the crude alkyl methacrylate from process step D2
(38) Phase separator with mixer optionally connected upstream
(39) Inflow for acid and water, optionally separated
(40) Extraction
(41) Distillation for recovering the alcohol (and methacrolein) for optional recycling
(42) Bottoms for disposal or further processing
(43) Optional recycling of the methacrylic acid-containing aqueous sidestream fraction from (41) into (25)
(44) Distillation column for separating high boilers (methacrylic acid-containing stream) for optional transfer to (32), (27) or (29))
(45) Distillation column for separating low boilers
(46) Distillation column for final purification of the alkyl methacrylate
(47) Alkyl methacrylate product stream With regard to the drawings, it should be noted that further components known to those skilled in the art may be included in addition to those for the execution of the process according to the invention. For example, each of the columns shown is generally equipped with a condenser.

It should also be noted that not every preferred embodiment is taken into account in the drawings.

The position of the inflow lines does not indicate their actual position, but merely indicates the apparatus in which the inflow line is fed.

The invention claimed is:

1. A process for producing alkyl methacrylate and optionally methacrylic acid, the process comprising:
producing methacrolein through a partial oxidation of isobutene and/or tert-butyl alcohol in a gas phase, in a first reaction in a reactor 1, and
converting the methacrolein by a partial oxidation in a gas phase to methacrylic acid, in a second reaction in a reactor 2,
separating unreacted methacrolein in reactor 2 in the second reaction from the methacrylic acid and oxidatively esterifying the unreacted methacrolein in a further oxidation in a reactor 4, in a liquid phase and in the presence of an alcohol, and
purifying by distillation and/or extraction crude methacrylic acid formed in reactor 2 and optionally further reacting with an alcohol in a reactor 3 under acid catalysis, to form the alkyl methacrylate.

2. A process for producing alkyl methacrylate and optionally methacrylic acid, the process comprising:
A) producing methacrolein from isobutene and/or tort-butanol in the presence of steam and a first oxygen-containing gas in a reactor 1, wherein a reaction takes place in a gas phase on a heterogeneous contact I, and wherein a methacrolein-containing process gas 1 is obtained,
B) transferring the process gas 1, which contains methacrolein and steam, from reactor 1, with supply of a second oxygen-containing gas and optionally, additional steam, to a reactor 2, wherein a reaction on a heterogeneous contact II takes place and a process gas 2 containing methacrylic acid and methacrolein is obtained,
C) separating the process gas 2 from B) by condensation or quenching, extraction, and/or distillation into a phase 3a comprising methacrylic acid and a phase 3b comprising methacrolein,
D1) oxidatively esterifying the methacrolein in the phase 3b obtained from step C) in a reactor 4 with a first alcohol in the presence of a third oxygen-containing gas and a heterogeneous noble metal-containing oxidation catalyst comprising one or more metals and/or metal oxides, wherein a mixture comprising an alkyl methacrylate, unreacted alcohol, methacrylic acid, and unreacted methacrolein is obtained as a liquid process stream 4,
D2) esterifying, under acid catalysis, the methacrylic acid in the phase 3a obtained from C), wherein the phase 3a is optionally first additionally purified, with a second alcohol in a reactor 3 on a contact III, and
D3) isolating the methacrylic acid obtained in phase 3a, including at least one distillation.

3. The process according to claim 2, wherein the process gas 1 is purified after A) by at least one distillation and/or extraction before being used as purified condensate and, after evaporation, as a component of the process gas 1 in B).

4. The process according to claim 2, wherein the second oxygen-containing gas in B) and/or the third oxygen-containing gas in D1) is a partially recycled gas stream.

5. The process according to claim 2, wherein the heterogeneous noble metal-containing oxidation catalyst used in D1) comprises one or more ultrafinely divided metals, having an average particle size of <20 nm, that is selected from the group consisting of gold, palladium, ruthenium, rhodium, and silver, and
wherein D1) is carried out in a liquid phase at a pressure of 1 to 100 bar.

6. The process according to claim 2, wherein the heterogeneous noble metal-containing oxidation catalyst used in D1) comprises one or more noble metals on one or more support materials based on silica, alumina, titanium dioxide, magnesium oxide, bismuth oxide, tellurium oxide, or other basic oxides from alkali metals and alkaline earth metals,
wherein the one or more support materials has a diameter from 10 μm to 10 mm.

7. The process according to claim 6, wherein the heterogeneous noble metal-containing oxidation catalyst further includes one or more further elements or oxides thereof selected from the group consisting of manganese, iron, cobalt, nickel, copper, zinc, lead, a lanthanoid, tellurium, antimony, bismuth, and an oxide thereof.

8. The process according to claim 2, wherein A) to D1) and D2), and optionally D3), are carried out in a continuous process.

9. The process according to claim 2, wherein the first alcohol in D1) is methanol, and wherein D1) is carried out with a molar ratio of methanol to methacrolein in a stationary reaction phase in the range from 1:1 to 50:1.

10. The process according to claim 2, wherein D1) is carried out in a liquid phase at a pressure in the range from 2 to 50 bar, a pH in the range from 3 to 10, and at a temperature in the range from 10 to 200° C.

11. The process according to claim 2, wherein the first alcohol in D1) and the second alcohol in D2) is in each case methanol.

12. The process according to claim 2, wherein crude products of D1) and D2) are purified directly from reactors 4 and 3, or
wherein the crude products of D1) and D2) are optionally first purified separately in one or two separate purifications, before being combined and purified together.

13. The process according to claim 2, wherein respective organic phases from D1) and D2) are purified separately in at least one distillation and/or one extraction before being combined.

* * * * *